US00PP13463P2

(12) United States Plant Patent
Vandenberg

(10) Patent No.: US PP13,463 P2
(45) Date of Patent: Jan. 7, 2003

(54) CHRYSANTHEMUM PLANT NAMED 'WATCH'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 15 days.

(21) Appl. No.: 09/900,103

(22) Filed: Jul. 9, 2001

(51) Int. Cl.[7] ..... A01H 5/00
(52) U.S. Cl. ..... Plt./289
(58) Field of Search ..... Plt./287, 289

*Primary Examiner*—Howard J. Locker
(74) *Attorney, Agent, or Firm*—C. A. Whealy

(57) ABSTRACT

A distinct cultivar of Chrysanthemum plant named 'Watch', characterized by its large quilled decorative-type inflorescences that are about 11.2 cm in diameter when grown as a disbud and about 8.8 cm in diameter when grown as a natural spray; attractive bright yellow-colored inflorescences with reddish brown centers; response time about 62 days when grown as a disbud and about 66 to 68 days when grown as a natural spray; dark green foliage; reddish brown-colored stems; and excellent postproduction longevity with inflorescences maintaining good substance and color for about three to four weeks in an interior environment.

2 Drawing Sheets

BACKGROUND OF THE INVENTION

The present invention relates to a new and distinct cultivar of Chrysanthemum plant, botanically known as *Chrysanthemum×morifolium* and hereinafter referred to by the name 'Watch'.

The new Chrysanthemum is a product of a planned breeding program conducted by the Inventor in Salinas, Calif. and Alva, Fla. The objective of the breeding program is to create new cut Chrysanthemum cultivars having inflorescences with desirable colors and good form and substance.

The new Chrysanthemum originated from a cross made by the Inventor in April, 1997, in Salinas, Calif., of a proprietary Chrysanthemum seedling selection identified as code number E611, not patented, as the female, or seed, parent with a proprietary Chrysanthemum seedling selection identified as 3499, not patented, as the male, or pollen, parent.

The cultivar Watch was discovered and selected by the Inventor as a flowering plant within the progeny of the stated cross in a controlled environment in Alva, Fla., in March, 1998. The selection of this plant was based on its desirable inflorescence color and good form and substance.

Asexual reproduction of the new Chrysanthemum by terminal cuttings taken in a controlled environment in Alva, Fla. since June, 1998, has shown that the unique features of this new Chrysanthemum are stable and reproduced true to type in successive generations.

SUMMARY OF THE INVENTION

Plants of the cultivar Watch have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Watch'.

These characteristics in combination distinguish 'Watch' as a new and distinct cultivar:

1. Upright cut Chrysanthemum that can be grown as a disbud or as a natural spray.

2. Large quilled decorative-type inflorescences that are about 11.2 cm in diameter when grown as a disbud and about 8.8 cm in diameter when grown as a natural spray.

3. Attractive bright yellow-colored inflorescences with reddish brown centers.

4. Response time about 62 days when grown as a disbud and about 66 to 68 days when grown as a natural spray.

5. Dark green foliage.

6. Reddish brown-colored stems.

7. Excellent postproduction longevity with inflorescences maintaining good substance and color for about three to four weeks in an interior environment.

Compared to plants of the female parent, the seedling selection identified as code number E611, plants of the new Chrysanthemum are about 8 to 10 cm taller and have larger inflorescences when grown as disbud. In addition, plants of the new Chrysanthemum and the female parent differ in ray floret color as plants of the female parent have white-colored inflorescences with cream-green centers.

Plants of the new Chrysanthemum and the male parent, the seedling selection identified as code number 3499, differ primarily in inflorescence form as inflorescences of the male parent are spooned daisy-types with three to four rows of ray florets and numberous disc florets. In addition, inflorescences of plants of the male parent do not have reddish brown centers.

Grown as a disbud, plants of the new Chrysanthemum can be compared to plants of the cultivar Mood, disclosed in U.S. Plant Pat. No. 12,935. In side-by-side comparisons conducted by the Inventor in Madrid, Cundinamarca, Colombia, South America, plants of the new Chrysanthemum and the cultivar Mood differ in inflorescence coloration as ray florets of the cultivar Mood are golden bronze in color. In addition, plants of the new Chrysanthemum have smaller inflorescences than plants of the cultivar Mood.

Grown as a natural spray, plants of the new Chrysanthemum can be compared to plants of the cultivar Estrella, disclosed in U.S. Plant Pat. No. 10,916. In side-by-side comparisons conducted by the Inventor in Madrid, Cundinamarca, Colombia, South America, plants of the cultivar Estrella are readily distinguishable from plants of the new Chrysanthemum by Esstrella's solid yellow-colored and spooned-tipped ray florets.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately described tha colors of the new Chrysanthemum.

The photograph on the first sheet comprises a side perspective view of a typical flowering stem of 'Watch' grown as a natural spray.

The photograph at the top of the second sheet comprises a close-up view of a typical flowering stem of 'Watch' grown as a natural spray.

The photograph at the bottom of the second sheet comprises a close-up view of a typical flowering stem of 'Watch' grown as a disbud.

DETAILED BOTANICAL DESCRIPTION

In the following description, color references are made to The Royal Horticultural Society Colour Chart except where general terms of ordinary dictionary significance are used. The aforementioned photographs and following observations and measurements describe plants grown in Madrid, Cundinamarca, Colombia, South America, under conditions which approximate commercial practice in a single-layer polyethylene-covered greenhouse. Two-week old rooted cutting were planted on Nov. 30, 2000 and received 14 long day/short nights followed by short day/long nights until flowering. Plants were grown as single-stem disbud and natural spray cut Chrysanthemums. During the production time, the following environmental conditions were measured: day temperatures, 19 to 24° C.; night temperatures, 4 to 12° C.; and light levels, 3,000 to 5,000 foot-candles. Measurements and numerical values represent averages for six to ten typical flowering stems and were taken about 9 to 10 weeks after the start of short days.

Botanical classification: *Chrysanthemum×morifolium* cultivar Watch.

Commercial classification: Quilled decorative-type cut Chrysanthemum.

Parentage:

*Female or seed parent*.—Proprietary *Chrysanthemum× morifolium* seedling selection identified as code number E611, not patented.

*Male or pollen parent*.—Proprietary *Chrysanthemum× morifolium* seedling selection identified as code number 3499, not patented.

Propagation:

*Type*.—Terminal tip cuttings.

*Time to rooting*.—About 10 to 14 days with soil temperatures of 18 to 21° C.

*Root description*.—Fine, fibrous and well-branched.

Plant description:

*Appearance*.—Herbaceous quilled decorative-type cut flower that can be grown as a disbud or natural spray.

*Flowering stem description*.—Aspect: Erect. Length: About 90 cm. Diameter (natural spray diameter): About 16.5 cm. Diameter (base of stem): About 5.5 mm. Internode length: About 4.8 cm. Texture: Densely pubescent; longitudinally ridged. Color: 146A heavily overlain with 187A.

*Foliage description*.—Arrangement: Alternate. Length: About 10.75 cm. Width: About 7.4 cm. Apex: Cuspidate. Base: Mostly truncate. Margin: Palmately lobed; sinuses mostly divergent. Texture: Upper and lower surfaces pubescent; smooth and leathery; veins prominent on lower surface. Color: Young foliage upper surface: 147A. Young foliage lower surface: Close to 147B. Mature foliage upper surface: 147A. Mature foliage lower surface: 147B. Venation, upper surface: 147A to 147B. Venation, lower surface: 147B. Petiole: Length: About 2.75 cm. Diameter: About 3.5 mm. Color, both surfaces: 147B.

Flowering description:

*Appearance*.—Decorative-type inflorescence form with elongated quilled-shaped ray florets. Inflorescences borne on terminals, arising from leaf axils. Disc and ray florets arranged acropetally on a capitulum.

*Flowering response*.—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 62 days later when grown as a disbud and about 66 to 68 days later when grown as a natural spray.

*Postproduction longevity*.—In an interior environment, flowering stems will maintain good color and substance for about three to four weeks in an interior environment after one week of cool storage.

*Quantity of inflorescences*.—When grown as a disbud, one per flowering stem, as the terminal inflorescence bud is the only one that is not removed. When grown as a natural spray, about 7 inflorescences per stem develop.

*Inflorescence size*.—Diameter: Disbud: About 11.2 cm. Natural spray: About 8.8 cm. Depth (height): Disbud: About 4.7 cm. Natural spray: About 3.2 cm. Diameter of disc: Disbud: About 3 mm, inconspicuous. Natural spray: About 1 mm, inconspicuous. Diameter of receptacle: Disbud: About 1.2 cm. Natural spray: About 8.5 mm.

*Inflorescence buds*.—Shape: Flattened sphere. Height: About 7 mm. Diameter: About 1 cm. Color: Close to 146A.

*Ray florets*.—Shape: Elongated, quilled. Length: Disbud: About 6 cm. Natural spray: About 4.7 cm. Width: Disbud: About 4 mm. Natural spray: About 3 mm. Corolla tube length: Disbud: About 5.4 cm. Natural spray: About 4.2 cm. Apex: Emarginate. Base: Fused. Texture: Satiny, smooth, glabrous; slightly longitudinally ridged. Aspect: Initially upright; when mature, about 45° from vertical; straight. Number of ray florets per inflorescence:

Disbud: About 354 arranged in numerous rows. Natural spray: About 272 arranged in numerous rows. Color: When opening: Towards base, 5A; towards apex, 5A overlain with close to 45A, which gives a reddish brown appearance to the center of the inflorescences. Mature, throat: 5A to 9A; color does not fade with development. Mature, tube: 5A to 6A; towards apex, 5A to 6A overlain with close to 45A; color does not fade with subsequent development.

*Disc florets*.—Shape: Tubular, elongated. Length: About 7 mm. Width: Apex: About 1.5 mm. Base: About 1 mm. Number of disc florets per inflorescence: Few, massed at center of receptacle, usually fewer than 5. Color: Immature: 144A to 144B. Mature: Apex: 9A; at apex, 9A overlain with 187A. Mid-section: 150D. Base: 155D.

*Peduncles* (*natural spray*).—Length: First peduncle: About 10.2 cm. Fourth peduncle: About 15.7 cm. Seventh peduncle: About 17.5 cm. Diameter: About 3 mm. Angle: About 30° from vertical. Strength: Very strong. Texture: Pubescent. Color: 146A heavily overlain with 187A.

*Reproductive organs*.—Androecium: Present on disc florets only. Anther color: Close to 12A. Amount of pollen: None observed. Gynoecium: Present on both ray and disc florets.

*Seed*.—Seed production has not been observed.

Disease/pest resistance: Resistance to pathogens and pests common to Chrysanthemums has not been observed on plants grown under commercial conditions.

Temperature tolerance: Plants of the new Chrysanthemum have demonstrated good tolerance to low temperatures of 5° C. Plants of the new Chrysanthemum do not tolerate high temperatures greater than 40° C.

It is claimed:

1. A new and distinct cultivar of Chrysanthemum plant named 'Watch', as illustrated and described.

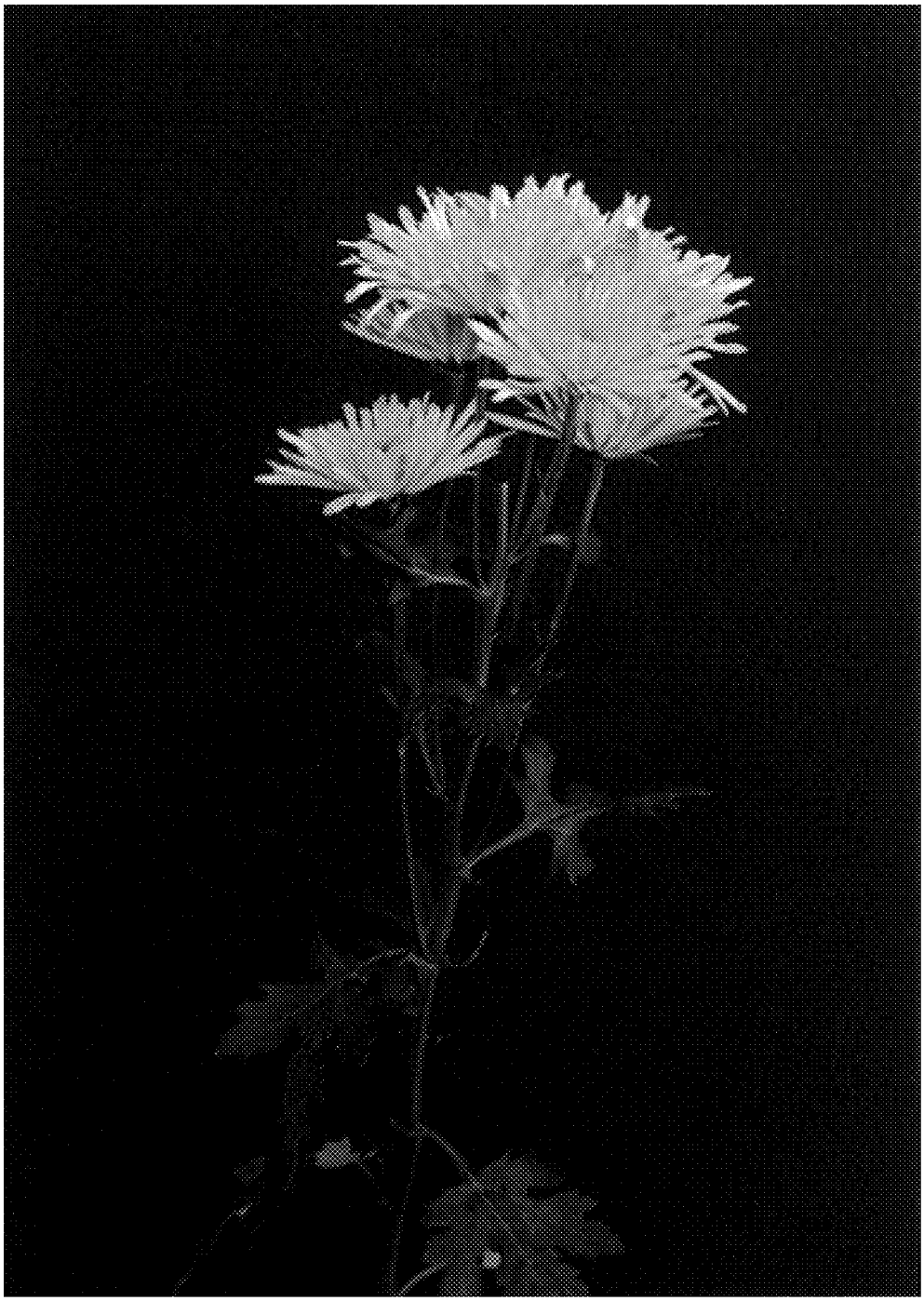

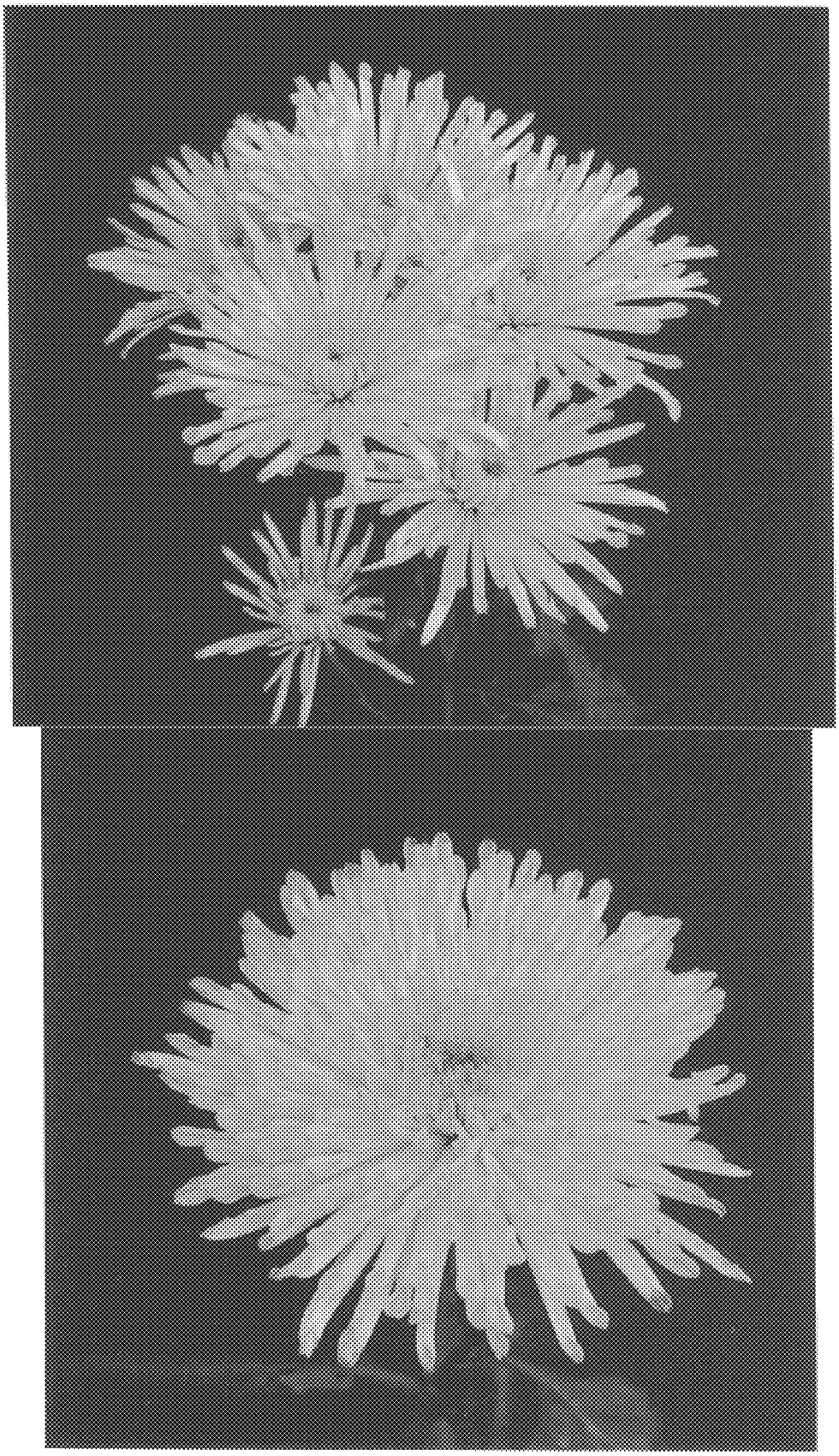

* * * * *